(12) United States Patent
Angel et al.

(10) Patent No.: US 7,651,475 B2
(45) Date of Patent: Jan. 26, 2010

(54) MICRONEEDLE TRANSPORT DEVICE

(75) Inventors: Aimee B. Angel, Atherton, CA (US); Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/972,726

(22) Filed: Jan. 11, 2008

(65) Prior Publication Data

US 2008/0319392 A1 Dec. 25, 2008

Related U.S. Application Data

(62) Division of application No. 10/238,844, filed on Sep. 9, 2002, now Pat. No. 7,429,258.

(60) Provisional application No. 60/338,425, filed on Oct. 26, 2001, provisional application No. 60/399,489, filed on Jul. 29, 2002.

(51) Int. Cl.
*A61M 31/00* (2006.01)

(52) U.S. Cl. .......................... 604/65; 604/151

(58) Field of Classification Search .............. 604/151, 604/20, 65–67, 132, 133, 140–147
See application file for complete search history.

(56) References Cited

U.S. PATENT DOCUMENTS

| 3,537 A | 4/1844 | Dodd |
|---|---|---|
| 1,934,046 A | 11/1933 | Demarchi |
| 2,088,780 A | 8/1937 | Follese |
| 2,763,935 A | 9/1956 | Whaley et al. |
| 2,945,496 A | 7/1960 | Fosdal |
| 3,505,993 A | 4/1970 | Lewes et al. |
| 3,568,735 A | 3/1971 | Lancaster |
| 3,659,600 A | 5/1972 | Merrill |
| 3,727,614 A | 4/1973 | Kniazuk |
| 3,738,493 A | 6/1973 | Cummins et al. |
| 3,814,097 A | 6/1974 | Ganderton et al. |
| 3,894,538 A | 7/1975 | Richter |

(Continued)

FOREIGN PATENT DOCUMENTS

DE 44 20 232 A1 6/1994

(Continued)

OTHER PUBLICATIONS

Lee, et al., "Fabrication and in Vitro Test of Microsyringe," *Sensors and Actuators*, 83:17-23 (2000).

(Continued)

*Primary Examiner*—Nicholas D Lucchesi
*Assistant Examiner*—Gerald Landry, II
(74) *Attorney, Agent, or Firm*—Hamilton, Brook, Smith & Reynolds, P.C.

(57) ABSTRACT

A transdermal transport device includes a reservoir for holding a formulation of an active principle, and an array of needles which have bores in fluid communication with the reservoir to facilitate transporting the formulation to and from the reservoir through the needles. The device also includes a first actuator which drives the array of needles into the body, and a second actuator which pumps the formulation between the reservoir and the body through the needles. The first actuator is reversible to withdraw the needles from the body.

23 Claims, 13 Drawing Sheets

U.S. PATENT DOCUMENTS

| | | | |
|---|---|---|---|
| 3,923,060 A | 12/1975 | Ellinwood, Jr. | |
| 3,964,482 A | 6/1976 | Gerstel et al. | |
| 4,140,109 A | 2/1979 | Savic et al. | |
| 4,394,231 A | 7/1983 | Nicolas | |
| 4,447,225 A | 5/1984 | Taff et al. | |
| 4,505,710 A | 3/1985 | Collins | |
| 4,619,652 A | 10/1986 | Eckenhoff et al. | |
| 4,685,466 A | 8/1987 | Rau | |
| 4,777,599 A | 10/1988 | Dorogi et al. | |
| 4,781,688 A | 11/1988 | Thoma et al. | |
| 4,808,156 A | 2/1989 | Dean | |
| 4,886,499 A | 12/1989 | Cirelli et al. | |
| 4,989,614 A | 2/1991 | Dejter, Jr. et al. | |
| 5,062,834 A | 11/1991 | Gross et al. | |
| 5,092,901 A | 3/1992 | Hunter et al. | |
| 5,156,591 A | 10/1992 | Gross et al. | |
| 5,225,750 A | 7/1993 | Higuchi et al. | |
| 5,250,023 A | 10/1993 | Lee et al. | |
| 5,262,128 A | 11/1993 | Leighton et al. | |
| 5,279,544 A * | 1/1994 | Gross et al. | 604/20 |
| 5,312,456 A | 5/1994 | Reed et al. | |
| 5,320,607 A | 6/1994 | Ishibashi | |
| 5,354,273 A | 10/1994 | Hagen | |
| 5,364,374 A | 11/1994 | Morrison et al. | |
| 5,389,222 A | 2/1995 | Shahinpoor | |
| 5,423,809 A | 6/1995 | Klicek | |
| 5,425,706 A | 6/1995 | Gross et al. | |
| 5,478,315 A | 12/1995 | Brothers et al. | |
| 5,478,328 A | 12/1995 | Silverman et al. | |
| 5,520,633 A | 5/1996 | Costin | |
| 5,527,288 A | 6/1996 | Gross et al. | |
| 5,533,995 A | 7/1996 | Corish et al. | |
| 5,578,495 A | 11/1996 | Wilks | |
| 5,591,139 A | 1/1997 | Lin et al. | |
| 5,599,345 A | 2/1997 | Edwards et al. | |
| 5,611,806 A | 3/1997 | Jang | |
| 5,649,423 A | 7/1997 | Sniegowski | |
| 5,697,901 A | 12/1997 | Eriksson | |
| 5,785,688 A | 7/1998 | Joshi et al. | |
| 5,827,216 A | 10/1998 | Igo et al. | |
| 5,843,016 A | 12/1998 | Lugnani et al. | |
| 5,848,991 A | 12/1998 | Gross et al. | |
| 5,855,801 A | 1/1999 | Lin et al. | |
| 5,879,326 A | 3/1999 | Godshall et al. | |
| 5,928,194 A | 7/1999 | Maget | |
| 5,928,207 A | 7/1999 | Pisano et al. | |
| 5,957,895 A | 9/1999 | Sage et al. | |
| 5,964,729 A | 10/1999 | Choi et al. | |
| 5,971,998 A | 10/1999 | Russell et al. | |
| 5,972,013 A | 10/1999 | Schmidt | |
| 5,983,136 A | 11/1999 | Kamen | |
| 5,997,501 A | 12/1999 | Gross et al. | |
| 6,027,459 A | 2/2000 | Shain et al. | |
| 6,048,337 A | 4/2000 | Svedman | |
| 6,050,988 A | 4/2000 | Zuck | |
| 6,056,716 A | 5/2000 | D'Antonio et al. | |
| 6,083,196 A | 7/2000 | Trautman et al. | |
| 6,090,790 A | 7/2000 | Eriksson | |
| 6,117,155 A | 9/2000 | Lee | |
| 6,123,684 A | 9/2000 | Deboer et al. | |
| 6,126,629 A | 10/2000 | Perkins | |
| 6,132,449 A | 10/2000 | Lum et al. | |
| 6,138,044 A | 10/2000 | Svedman | |
| 6,144,869 A | 11/2000 | Berner et al. | |
| 6,148,232 A | 11/2000 | Avrahami | |
| 6,183,434 B1 | 2/2001 | Eppstein | |
| 6,187,210 B1 | 2/2001 | Lebouitz et al. | |
| 6,230,051 B1 | 5/2001 | Cormier et al. | |
| 6,233,471 B1 | 5/2001 | Berner et al. | |
| 6,246,904 B1 | 6/2001 | Murdock | |
| 6,254,580 B1 | 7/2001 | Svedman | |
| 6,256,533 B1 | 7/2001 | Yuzhakov et al. | |
| 6,317,630 B1 | 11/2001 | Gross et al. | |
| 6,319,320 B1 | 11/2001 | Mendez-Gallon | |
| 6,375,624 B1 | 4/2002 | Uber, III et al. | |
| 6,408,204 B1 | 6/2002 | Hirschman | |
| 6,440,096 B1 * | 8/2002 | Lastovich et al. | 604/27 |
| 6,565,532 B1 | 5/2003 | Yuzhakov et al. | |
| 6,611,707 B1 | 8/2003 | Prausnitz et al. | |
| 6,678,556 B1 | 1/2004 | Nolan et al. | |
| 6,743,211 B1 | 6/2004 | Prausnitz et al. | |
| 6,918,901 B1 * | 7/2005 | Theeuwes et al. | 604/500 |
| 2002/0077584 A1 * | 6/2002 | Lin et al. | 604/21 |
| 2003/0028172 A1 | 2/2003 | Epstein et al. | |

FOREIGN PATENT DOCUMENTS

| | | |
|---|---|---|
| EP | 0302278 A1 | 2/1989 |
| FR | 757501 | 12/1933 |
| GB | 912194 | 12/1962 |
| GB | 2 335 990 A | 10/1999 |
| WO | WO 93/17754 | 9/1993 |
| WO | WO 94/23777 | 10/1994 |
| WO | WO 95/07722 | 3/1995 |
| WO | WO 96/14026 | 5/1996 |
| WO | WO 96/37155 | 11/1996 |
| WO | WO 96/37256 | 11/1996 |
| WO | WO 97/48440 | 12/1997 |
| WO | WO 97/48442 | 12/1997 |
| WO | WO 99/62576 | 12/1999 |
| WO | WO 99/64580 | 12/1999 |
| WO | WO 00/05166 | 2/2000 |
| WO | WO 00/05339 | 2/2000 |
| WO | WO 00/16833 | 3/2000 |
| WO | WO 00/27473 | 5/2000 |
| WO | WO 00/67647 | 11/2000 |
| WO | WO 00/74763 A2 | 12/2000 |
| WO | WO 00/74765 A1 | 12/2000 |
| WO | WO 00/74766 A1 | 12/2000 |
| WO | WO 00/78212 A1 | 12/2000 |
| WO | WO 01/79706 A2 | 10/2001 |
| WO | WO 02/055128 A2 | 7/2002 |
| WO | WO 02/100469 A2 | 12/2002 |

OTHER PUBLICATIONS

Ebbing, "Electrochemistry," In *General Chemistry. 4th ed.*, (MA, TX, IL, CA, NJ, Canada, Geneva: Houghton Mifflin Company), pp. 808, 810-811 (1993).

* cited by examiner

MICRONEEDLE TRANSPORT DEVICE

RELATED APPLICATION(S)

This application is a divisional of U.S. application Ser. No. 10/238,844, filed Sep. 9, 2002, now U.S. Pat. No. 7,429,258 which claims the benefit of U.S. Provisional Application No. 60/338,425, filed on Oct. 26, 2001 and U.S. Provisional Application No. 60/399,489 filed Jul. 29, 2002.

The entire teachings of the above application(s) are incorporated herein by reference.

BACKGROUND OF THE INVENTION

Delivery of drugs to a patient is performed in a number of ways. For example, intravenous delivery is by injection directly into a blood vessel; intraperitoneal delivery is by injection into the peritoneum; subcutaneous delivery is under the skin; intramuscular is into a muscle; and orally is through the mouth. One of the easiest methods for drug delivery, and for collection of body fluids, is through the skin.

Skin is the outermost protective layer of the body. It is composed of the epidermis, including the stratum corneum, the stratum granulosum, the stratum spinosum, and the stratum basale, and the dermis, containing, among other things, the capillary layer. The stratum corneum is a tough, scaly layer made of dead cell tissue. It extends around 10-20 microns from the skin surface and has no blood supply. Because of the density of this layer of cells, moving compounds across the skin, either into or out of the body, can be very difficult.

The current technology for delivering local pharmaceuticals through the skin includes both methods that use needles or other skin piercing devices and methods that do not use such devices. Those methods that do not use needles typically involve: (a) topical applications, (b) iontophoresis, (c) electroporation, (d) laser perforation or alteration, (e) carriers or vehicles, which are compounds that modify the chemical properties of either the stratum corneum and/or the pharmaceutical, (f) physical pretreatment of the skin, such as abrasion of the stratum corneum (e.g. repeatedly applying and removing adhesive tape), and (g) sonophoresis, which involves modifying the barrier function of stratum corneum by ultrasound.

Topical applications, such as a patch, or direct application of a pharmaceutical to the skin, depend on diffusion or absorption through the skin. These methods of transdermal transport are not widely useful because of the limited permeability of the stratum corneum. Although techniques such as those listed above have been developed to enhance the effectiveness of topical applications, topical applications still cannot provide optimum transdermal transport.

On the other hand, invasive procedures, such as use of needles or lances, effectively overcome the barrier function of the stratum corneum. However, these methods suffer from several major disadvantages: pain, local skin damage, bleeding, and risk of infection at the injection site, and creation of contaminated needles or lances that must be disposed of. These methods also usually require a trained administrator and are not suitable for repeated, long-term, or controlled use.

Additionally, drug delivery through the skin has been relatively imprecise in both location and dosage of the pharmaceutical. Some of the problems include movement of the patient during administration, delivery of incomplete dosages, difficulties in administering more than one pharmaceutical at the same time, and difficulties in delivering a pharmaceutical to the appropriate part of the skin. Drugs have traditionally been diluted to enable handling of the proper dosages. This dilution step can cause storage as well as delivery problems. Thus, it would be advantageous to be able to use small, precise volumes of pharmaceuticals for quick, as well as long-term, delivery through the skin.

Some have proposed using microneedle devices to provide more effective transport rates than topical applications because they penetrate through the stratum corneum. At the same time, they are almost entirely painless because the microneedles are relatively small and do not penetrate deep enough to impinge subdermal nerves. These devices may also be used in conjunction with means for controlling transport rates, such as pumps or permeable membranes.

SUMMARY

A continuing need exists in the field for an effective, multiapplication, transdermal microneedle transport system, which provides painless, precision insertion and controlled, programmable transport at commercially viable costs.

The microneedle transport device of the present invention includes, at its most basic level, one or more microneedles connected to at least one reservoir. The microneedles can be provided in one or more rows or arrays. The arrays can be arranged in a Cartesian or circular pattern. A system for delivering substances to or withdrawing fluids from a patient can further include one or more actuators, pumps, and/or sensors. These elements can be combined in a variety of ways to produce systems with different attributes for delivery and/or collection of substances or information through the skin.

The microneedle transport device disclosed herein may have several applications, including but not limited to drug delivery, sampling, and biological monitoring. In application as a drug delivery device, each reservoir is filled with one or more drugs to be delivered. In sampling, each reservoir is initially empty and then filled with biological material, such as interstitial fluid. In monitoring, the device is adapted with sensors to monitor, for example, the concentration of a compound, such as glucose, in fluid that has been withdrawn, or with some receptor on the needle going into the skin (i.e., the fluid doesn't have to be withdrawn necessarily).

In one embodiment, a transdermal transport device includes a reservoir for holding a formulation of an active principle, and an array of needles which have bores, or hollow pathways, in fluid communication with the reservoir. The device also includes a first actuator which drives the array of needles into the body, and a second actuator which pumps the formulation between the reservoir and the body through the needles, i.e., to and/or from the reservoir. The first actuator is reversible in some instances to withdraw the needles from the body. The first actuator may function as an applicator for the second actuator. Optionally, there can be another applicator that places the first and second actuators on the patient's skin.

In some embodiments the microneedles are adapted to puncture and penetrate the outer layers of the skin (the stratum corneum), at a minimum, of a biological body such as a human patient and facilitate transport of material or information between the device and a target area.

In particular embodiments, the second actuator pumps the formulation into the body to provide controlled, programmable transport of the formulation. When used for drug delivery, the transdermal transport device provides precise delivery of pharmaceuticals to a patient, including customization of doses to the needs of the particular patient. In certain embodiments, pain is reduced or absent in a patient due to the shape of the microneedles and the depth of their insertion into the skin.

In some embodiments, the second actuator is reversible to draw the formulation into the reservoir. For example, the formulation can be a fluid sample collected from a patient. The transport device can include a sensor to monitor the status of the patient, such as by monitoring the glucose concentration in the sample collected from the patient. This embodiment can be combined with the pharmaceutical delivery, such as for delivering insulin to a patient based on the glucose concentration determined by the device.

Operation of the transport device may be manual or automatic, or some combination thereof. The first and/or second actuators can be vapor generators, chemical reaction actuators, mechanical, or magnetic. The actuators can operate by an electrochemical process that is, for example, initiated by twisting a part of the actuator, or by applying pressure to the actuator. Optionally, the transport device may have sensing capabilities and oscillators to assist in insertion of the needles through the stratum corneum. One or more programmable microprocessors or controllers may also be used to control the various components of the device. For example, one controller can coordinate the operation of the first and second actuators. Optionally, one controller can control the operation of the first actuator, while another controller operates the second actuator. A controller may be associated with an applicator that is used to place the first and second actuators on the patient's skin. Thus, the transport device can include a closed-loop system to control drug delivery based on feedback information from monitoring, and/or sampling, to achieve programmed medication. For example, interstitial fluid may be withdrawn from a patient, glucose content measured, and the appropriate amount of insulin delivered.

In yet other embodiments, the second actuator, reservoir and microneedles are contained in a cartridge, and the first actuator is contained in a control unit. The two units can be separate units which can be connected together.

In another embodiment, a transdermal transport device includes a reservoir for holding a formulation of an active principle, and an array of needles, as described above. The device includes a first actuator which drives the array of needles into a biological body, and contracts to withdraw the needles from the body, and a second actuator with a chamber which changes in volume to facilitate pumping the formulation between the reservoir and the body through the needles.

In yet another embodiment, in addition to a reservoir and an array of needles which have bores in fluid communication with the reservoir, a transdermal transport device includes a vapor generator actuator which pumps the formulation between the reservoir and a biological body through the bore of the needles.

Embodiments may have one or more of the following advantages. The microneedle transport device disclosed here further presents the advantages of low manufacturing costs, and high efficiency. Particularly in regards to ease of use, the automated/mechanical system of the microneedle device reduces the error and uncertainty usually introduced by manual application. Very little (if any) pain, local damage, bleeding, or risk of infection is caused by the microneedles. Additionally, no special training or expertise is required to use the microneedle transport device. The device may further be adapted for disposable single-use, partial or full reuse, short or long-term use, or continuous or intermittent transport, or some combination thereof. The device provides for a controllable and precise drug delivery to a location below the skin of the patient. That is, any desirable delivery profile can be set, for example, constant or intermittent, for delivery to a desired location. The device can provide on-demand delivery, for example, by pushing a button, when a patient desires some sort of pain control. Since a precise amount of volume of drug can be delivered, there is a low volume of wasted drug. In addition to delivering a precise volume of drug with a variety of delivery profiles, the device is able to deliver a range of drugs. For example, the formulation may be a liquid, or a non-liquid that is reconstituted at delivery, or some combination thereof. The device is small and portable, and the geometry of the device makes it comfortable to wear.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
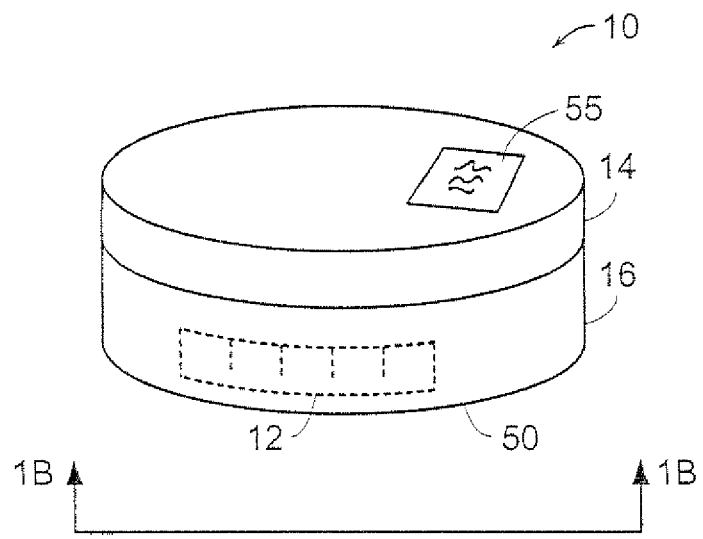
FIG. 1A is a perspective view of a transdermal transport device in accordance with the invention.

A description of preferred embodiments of the invention follows.

Referring to FIGS. 1A-1D, there is shown a transdermal transport device indicated by the reference numeral 10. The device 10 includes an array of microneedles 12, that may be bent or straight, for piercing the outer layers of skin of the patient and for delivering a formulation of an active principle such as pharmaceuticals through the skin to provide accurate delivery of the pharmaceuticals to the patient. Moreover, because of the shape and size of the needles and the minimal depth of penetration of the needles, contact between the needles and the nerve endings beneath the outer layer of the skin is minimized so that pain is reduced or absent in the patient. The pharmaceutical may be a liquid formulation, or it may be one or more non-liquid drugs that are reconstituted just before delivery.

The transport device 10 includes a control unit 14 and a base unit or cartridge 16. The device 10 may be fully disposable, or a portion of the device may be disposable. For example, the base unit 16 may be disposable, while the control unit functions as a reusable applicator.

Figure 1B:
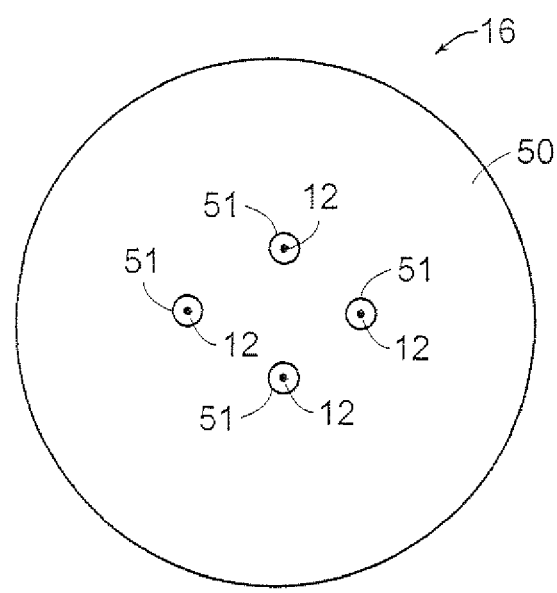
FIG. 1B is a bottom view of the transdermal transport device of FIG. 1A along the line 1B-1B.
Figure 1C:
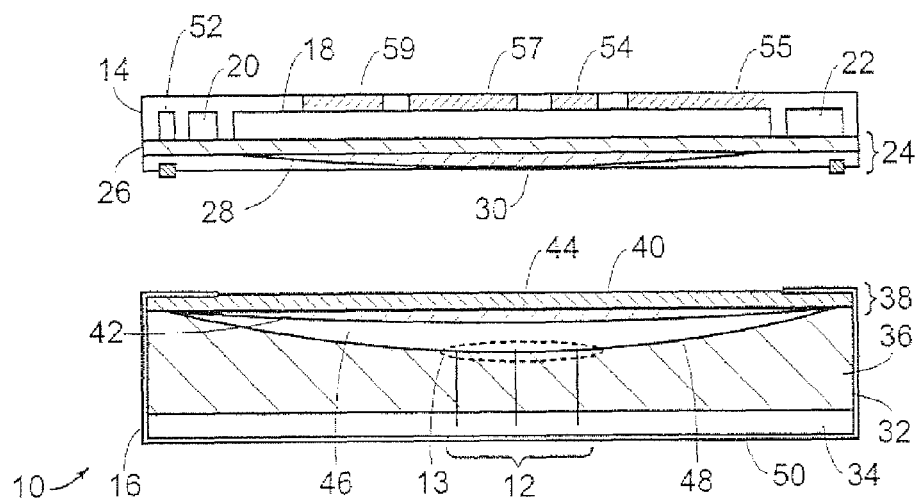
FIG. 1C is a cross-sectional side view of a base unit and a control unit of the transdermal transport device of FIG. 1A shown as separate units.
Figure 1D:
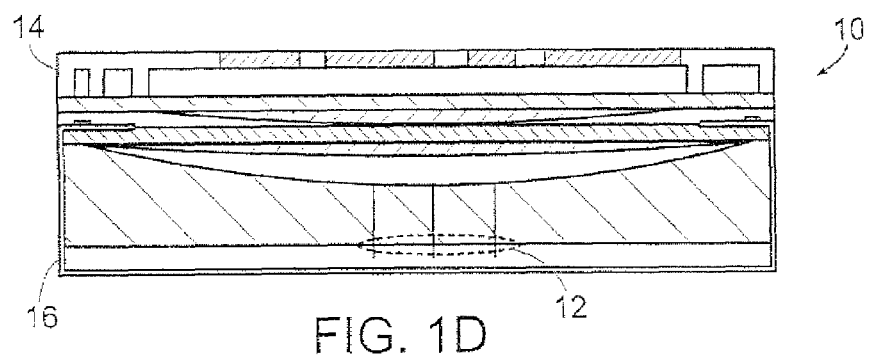
FIG. 1D is a cross-sectional side view of the control unit and the base unit of the transdermal transport device of FIG. 1A connected together.

The two units 14 and 16 are shown as separate units in FIG. 1C. The units 14 and 16 are connected together as illustrated in FIG. 1D by a simple twisting motion, or clicking the units into place. The control unit 14 is provided with electronics 18, power components 20 such as batteries and/or supercapacitors, and a processor 22. A drive actuator 24 of the control unit 14 includes a heater 26 and a flexible membrane 28 that define an expansion chamber 30 therebetween. Alternatively, the membrane 28 may be plastically deformed, so that is not flexible.

The base unit 16 includes a rigid housing 32 in which there is a rubber plenum 34 and a supportive foam 36 positioned on top of the plenum. The base unit is also provided with a reservoir actuator 38 that includes a heater 40 and a flexible membrane 42 both of which define an expansion chamber 44 between the two. There is also a reservoir 46 located between the flexible membrane 42 and a rigid shell 48. Attached to the shell 48 is the set of microneedles 12. Each microneedle 12 is provided with a bore, or hollow pathway, through which a pharmaceutical held in the reservoir 46 is transmitted from the reservoir to a patient. Alternatively, the reservoir can hold a sample collected from the patient through the microneedles 12. Some or all of the components of the control unit 14 can in certain implementations be included in the base unit 16. Note that the reservoir 46 may function as a separate vial that is detachable from the base unit 16. As such, the reservoir 46 may be pre-loaded with the formulation and then placed into the base unit 16 prior to delivery.

The base unit 16 also includes a cover 50 with openings 51 through which the microneedles 12 can extend from the bottom of the base unit. In use, the needles 12 are rotated such that they align with the openings 51. When the device 10 is not in use, the microneedles 12 are rotated in a manner such that they cannot extend through the bottom to prevent accidental exposure to the microneedles. This minimizes or eliminates contamination of the microneedles and accidental contact between the needles and a patient or medical clinician.

In the device 10, the actuators 24 and 38 operate as vapor generators. The heaters 26 and 40 heat a liquid such as water contained in the respective expansion chambers 30 and 44. The liquid changes to a vapor with a consequent volume expansion of the chambers which causes the respective membranes 28 and 42 to move outward. In particular embodiments, the volume of the liquid water is about 500 nl to 5 µl. The temperature of vaporization of water is 100° C., and at that temperature the latent heat of vaporization is 2.25 kJ/kg. Thus for 1 µl of liquid water, the steam volume becomes approximately 1.7 ml.

Accordingly, outward movement of the membrane 28 causes the membrane to push the actuator 38, the reservoir 46, and the microneedles 12 away from the control unit 14. As this occurs, the shell 48 compresses the supportive foam 36 and the microneedles 12 moves through the supportive foam 36 and the rubber plenum 34.

Similarly, when the actuator 38 is activated, the flexible membrane 42 is pushed outward, thereby expelling the pharmaceutical held in the reservoir 46 through the microneedles 12. When this process is operated in reverse, a liquid such as a sample from a patient or a drug from a vial, can be collected into the reservoir 42.

The transport device 10 shown in FIGS. 1A and 1B can include sensors that measure pressure or temperature. Additionally or alternatively, the device 10 is provided with a chemical and/or glucose sensor, as well as an impedance sensor 52.

The impedance sensor 52 is used to indicate when the microneedles have sufficiently penetrated into the skin. A piezoelectric or a speaker 54 is also used to provide audible, perhaps verbal, indications to the user, and a display 55 positioned on top of the control unit 15 provides visual information to the user.

The device 10 is used to deliver precise amounts of drugs as needed by a patient. Information relating to the patient can be relayed through an associated computer to the device 10 and the applicator 12 via a communication card 57. Additionally or alternatively, the communication card can be a Bluetooth card which provides wireless communication capabilities.

A procedure for using the device 10 is illustrated in the series of FIGS. 2A-2D. Initially, a user, such as a patient or a medical clinician, connects the control unit 14 with the base unit 16, rotates the cover 50 of the device 10 to an open state, and attaches the bottom of the base unit 16 to a drug vial 100 (FIG. 2A) which holds a drug that is to be delivered to the patient. The drug vial 100 includes a Type I or Type II high purity glass container 102 which holds the drug. The vial 100 could also be made of a polymer material or stainless steel. The drug is sealed in the glass container 102 with a silicon based rubber plenum 104 having a thickness of about 50 µm to 2 mm, preferably less than 300 µm. The plenum could be made of polymer or laminated rubber, as well. The rubber plenum 104 is secured to the glass container with an aluminum or stainless steel ring cap 106. The ring cap 106 has a thickness of about 50 µm to 300 µm, preferably 100 µm. The inner opening of the ring 106 provides access to the rubber plenum 104 for the device 10.

The user then flips the device 10 upside down (FIG. 2A), and activates the device 10 to initiate the transport process, thereby turning on the actuator 24 of the control unit 14 such that the expansion of the chamber 30 causes the actuator 38, the reservoir 46, and the microneedles 12 to move towards the drug vial 100. The microneedles 12 move through the supportive foam 36 and the rubber plenum 34 until they extend through the openings 51 (FIG. 1B) in the cover 50 at the bottom of the device 10 and into the pharmaceutical contained in the vial 100.

Next, the processor 22 activates the actuator 38 to evacuate air or an inert gas, initially contained in the reservoir 46, by dispelling it into the vial 100. Once the processor 22 detects that the membrane 42 is fully expanded, it shuts off the actuator 38. As the vapor in the expansion chamber 44 condenses, the volume of the chamber 44 decreases with a consequent increase in volume of the reservoir 46 which draws the pharmaceutical through the microneedles 12 into the reservoir. Then, the processor 22 turns off the actuator 24 so that the actuator 38, the filled drug reservoir 46, and the microneedles 12 move back to their initial state, as the supportive foam 36 pushes against the shell 48. Note that in some embodiments, rather than filling the drug reservoir 46 with the drug vial 100, the drug reservoir comes preloaded with a pharmaceutical. Note also that as the microneedles 12 move back to their retracted state, the plenum 34 acts as a wipe to clean the outer surfaces of the microneedles 12.

Figure 2A:
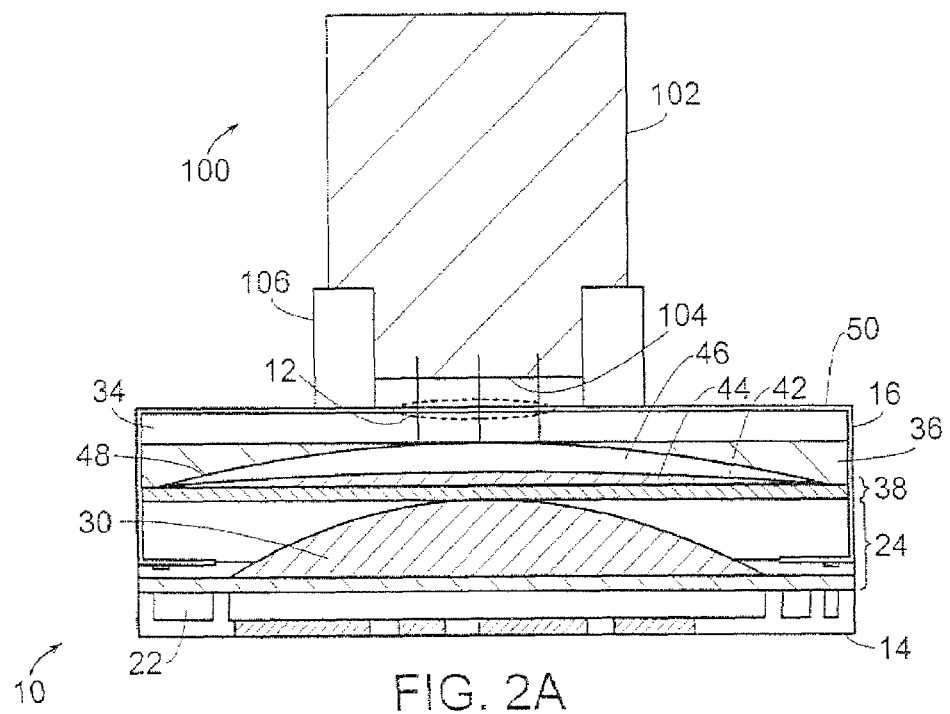
FIGS. 2A-2D illustrate a sequence of steps performed to draw a drug from a drug vial and inject the drug into a patient with the transdermal transport device shown in FIGS. 1A-1D.
Figure 2B:
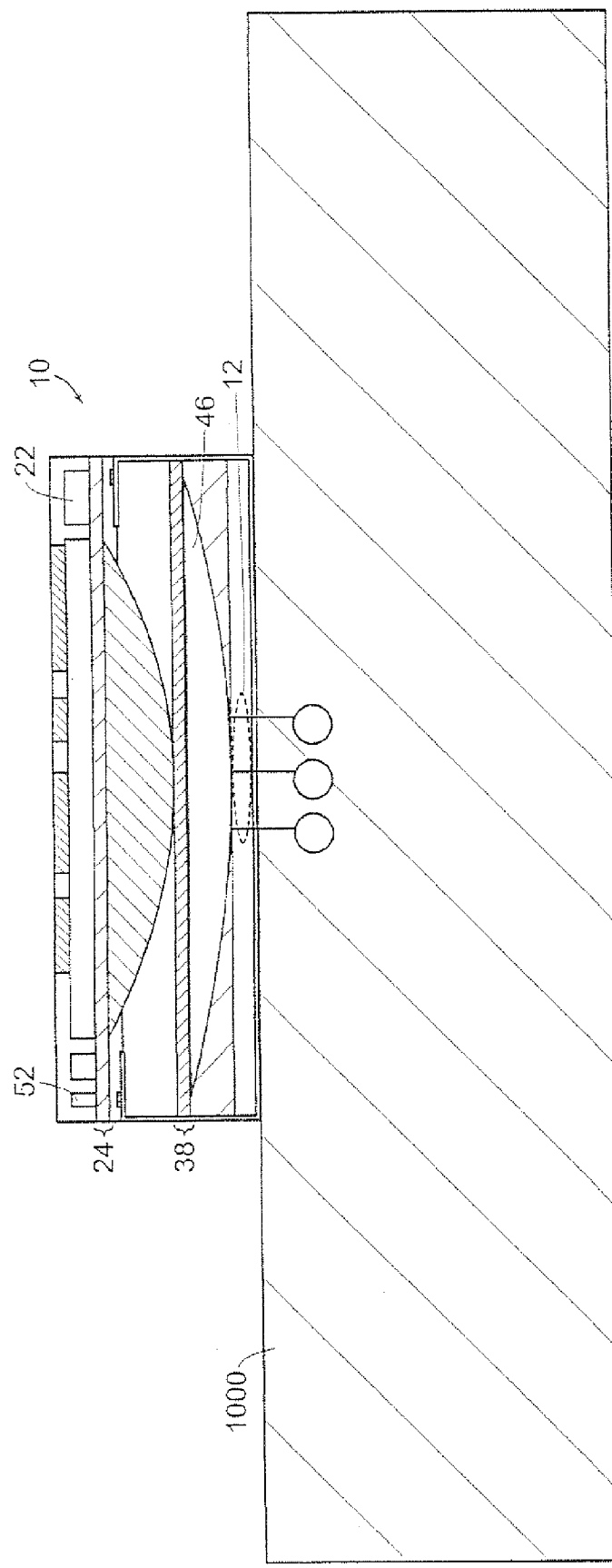

The user then removes the device 10 from the drug vial 100 and places the device on the patient's skin 1000. The device 10 is secured to the skin 1000 by any suitable means such as, for example, an adhesive or a strap. Once again, the processor 22 activates the actuator 24 to inject the microneedles 12 into the skin (FIG. 2B). Once the microneedles 12 contact the skin 1000, they continue to move in the same direction approximately 50 μm to several mm below the surface of the skin, thereby penetrating the skin. In one embodiment, the penetration depth is approximately 200 μm. The extent of movement in this direction is dictated by the depth of the stratum corneum at the site where the microneedles 12 penetrate the skin. As stratum corneum depth varies, the control unit 14 uses the impedance sensor 52 to determine when the stratum corneum has been traversed. The impedance sensor 52 measures impedance of electric current flow between two of the microneedles 12. Impedance is high in the stratum corneum, and drops dramatically in the portion of the dermis just below the stratum corneum (see, e.g., FIG. 10 which shows a drop of approximately three orders of magnitude). The sensor 52 reads the change in impedance as the microneedles 12 penetrate into the skin, and movement is stopped when the impedance drops by an order of magnitude. Additionally or alternatively, there can be a hard mechanical stop that prevents the microneedles from penetrating too deeply.

Figure 2C:
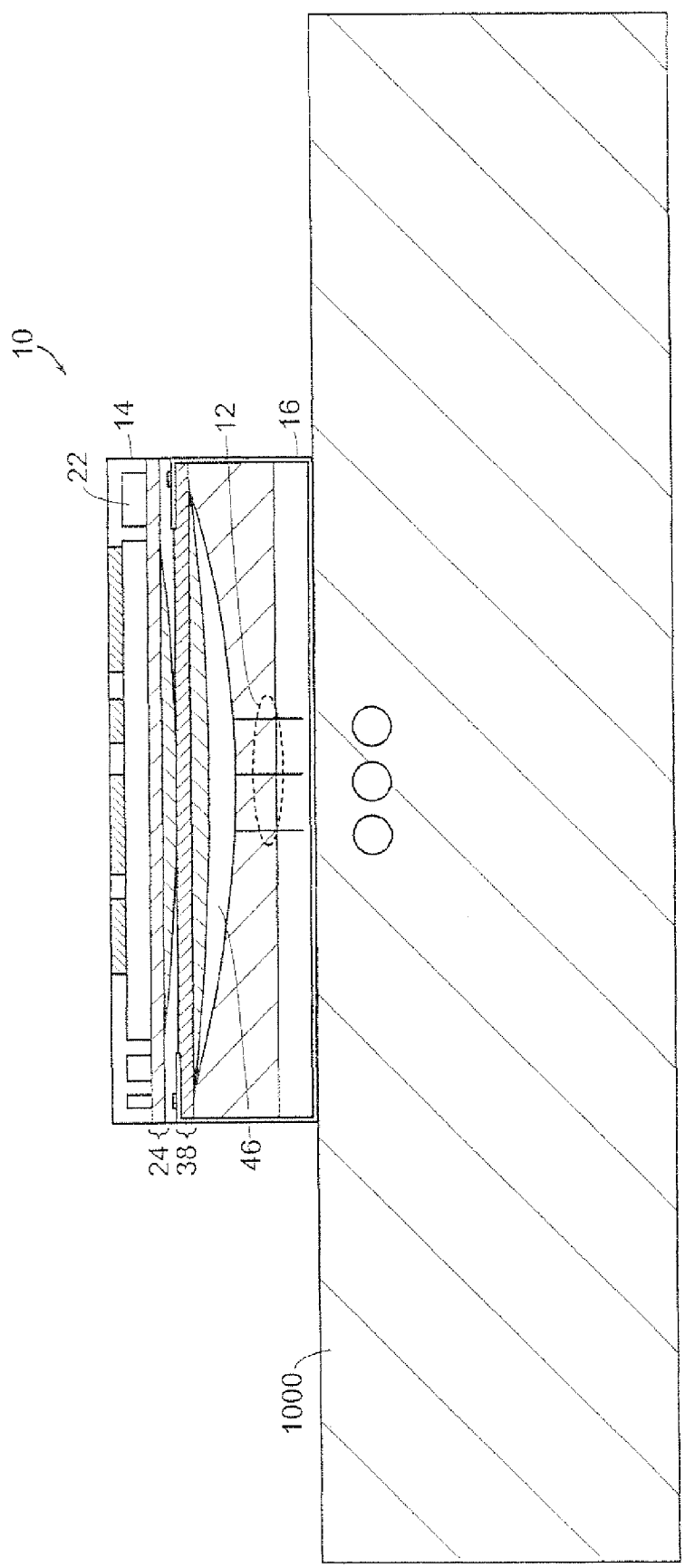
Figure 2D:
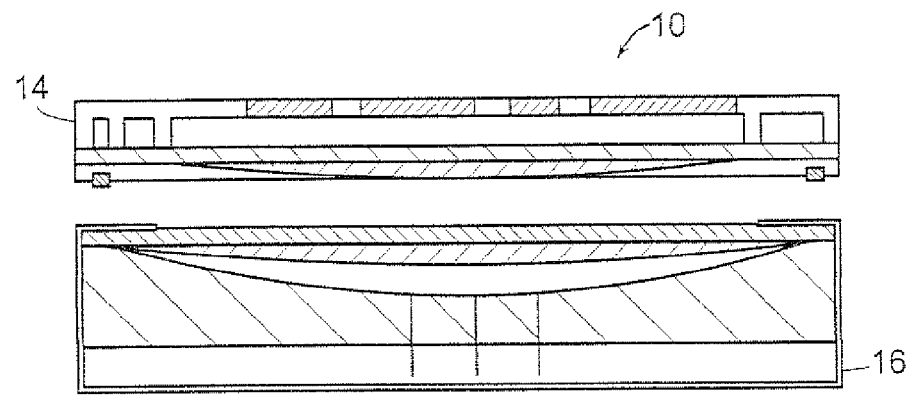

The actuator 38 is then turned on by the processor 22 to inject the drug from the reservoir 46 through the microneedles 12 into the skin 1000. The processor 22 then turns off the actuator 24 to withdraw the microneedles 12 from the skin (FIG. 2C). After the microneedles are fully retracted, the other actuator 38 is deactivated such that the reservoir 46 fills with air. Subsequently, the user removes the device 10 from the skin and disconnects the control unit 14 from the base unit 16 (FIG. 2D) and discards the base unit.

Figure 3:
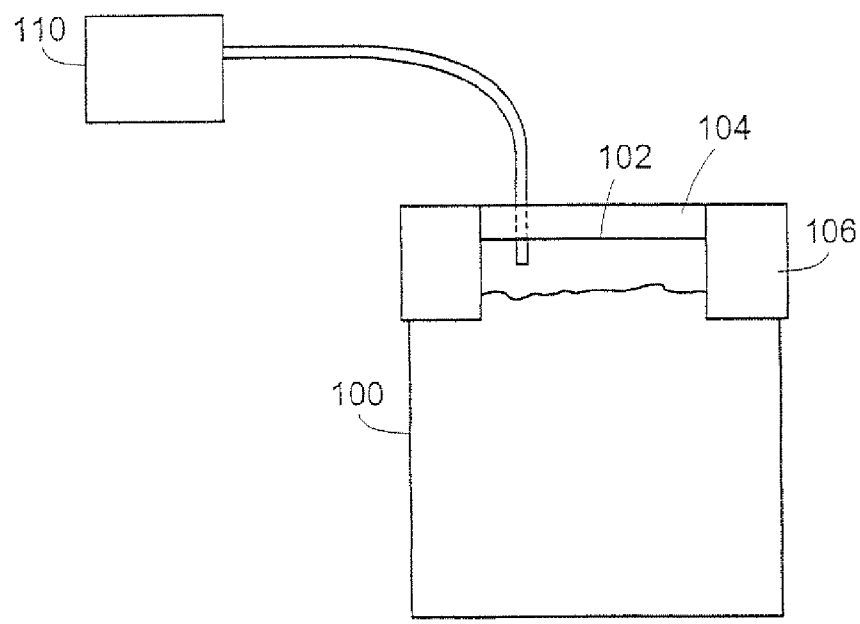
FIG. 3 is a view of an alternative embodiment with an external supply of inert gas to replace the contents removed from a drug vial.

In another application, the actuator 38 is activated before the device 10 is attached to the vial 100 to evacuate air from the reservoir 46. The device 10 is then attached to the vial 100, the reservoir 46 is filled with the pharmaceutical, and the device 10 is removed from the vial 100. As shown in FIG. 3, the drug removed from the vial 100 can be replaced with an inert gas, such as nitrogen, provided by a gas supply 110. Regardless of how the inert gas is transmitted to the vial 100, the gas prevents the pharmaceutical from oxidizing in air.

As mentioned earlier, the same device 10 can be used for collecting fluid, such as interstitial fluid, from the dermis. For collection to occur, the reservoir 46 must first be evacuated. This is accomplished by activating the actuator 38 which causes the expansion chamber 44 to expand and hence to move the membrane 42 downward to expel any air in the reservoir 46. Upon penetration of the microneedles into the skin, the expansion chamber 44 of the actuator 38 is contracted to allow the drug vial 40 to create a vacuum inside the reservoir 46, which draws fluid through the microneedles into the reservoir 46.

Thus, the actuator 38 disclosed herein acts as a pump which facilitates pumping a drug through the microneedles into the skin or collecting a sample from the patient. The actuator 38 can be used to create a vacuum within the reservoir 46 before the device 10 is placed against the skin. In sum, the actuator 38 provides controlled, programmable transport to and from the target site.

The various features of the transport device 10 will now be described in greater detail.

In the present application, the term "microneedle" is intended to be construed as singular or plural, unless specifically modified by a term indicating the number of microneedles. Microneedles disclosed herein may be porous or non-porous, uniform or of varying diameters or cross-sectional geometries, or some combination thereof. Hollow microneedles with uniform diameter are sometimes referred to as microtubes. As used herein, the term "microneedle" refers to both microtubes and any other kind of microneedle as described previously. Additionally, microneedles may also have openings at either or both ends, as well as, on the side-walls at various and/or multiple positions along the length, or any combination thereof. Further, either or both ends of the microneedle may be flat, tapered to a point, rounded, or beveled from one or more sides, as described below.

Figure 4:
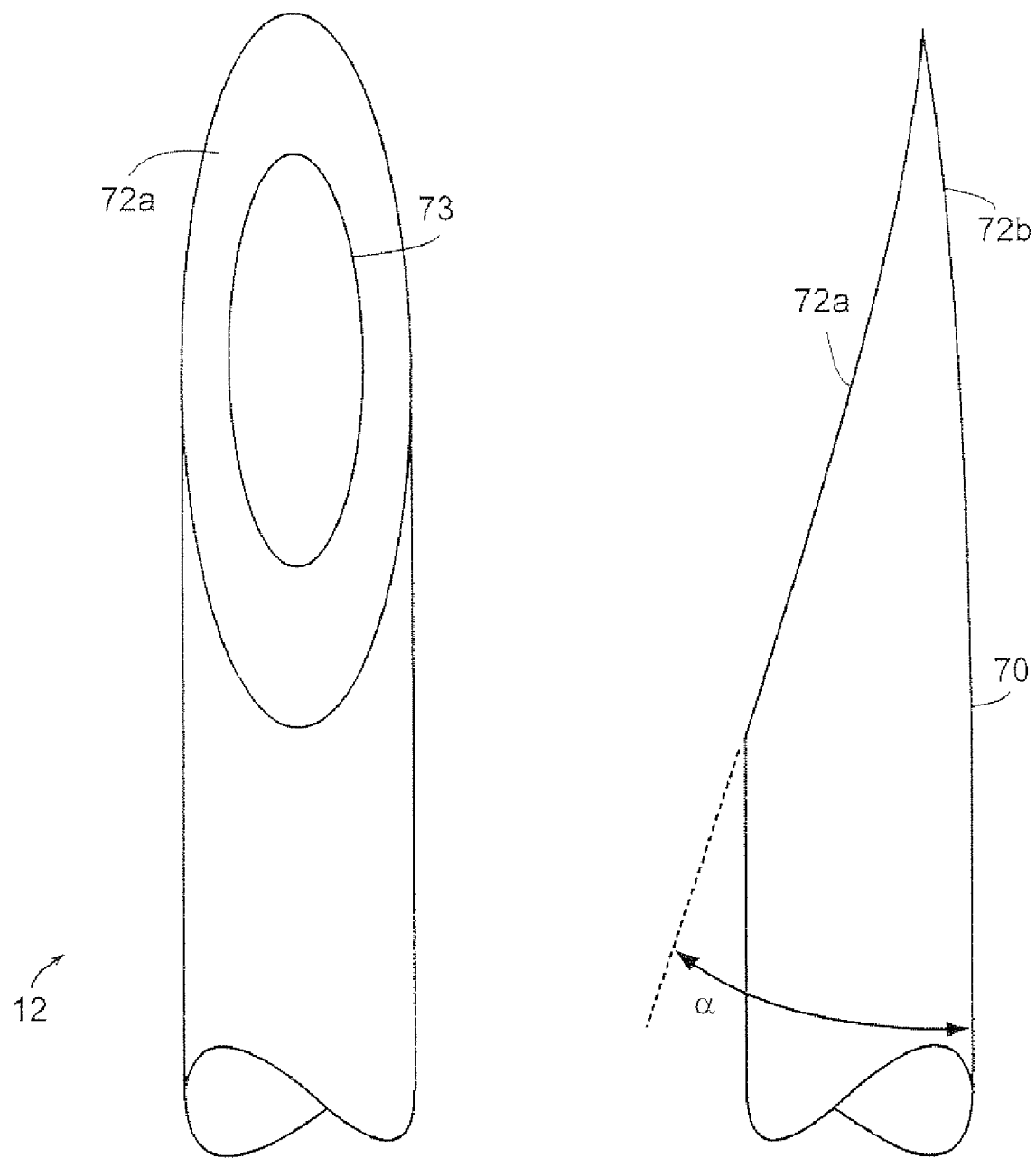
FIG. 4 is a close-up view of a tip of a microneedle of the transdermal transport device of FIGS. 1A-1D.

As shown in FIG. 4, each microneedle 12 has a tip 70 cut at an angle, $\alpha$, of approximately 10° to 60°, to provide a slanted surface 72a surrounding an opening 73 of the bore through the microneedle. This surface 72a and/or the outer surface 72b can be beveled. The beveled tip has many advantages. It reduces the trauma to the skin; it further reduces any pain felt by the subject; it prevents coring of the tissue into the microneedle; and it decreases the amount of force required for penetration into the skin. Particularly, in regards to coring, sharp tipped microneedles having a small inner diameter are less likely to accumulate tissue within the hollow opening, thereby avoiding transport blockage.

The illustrated embodiment has four microneedles 12 (FIGS. 1A and 1B), but there can be ten microneedles or more.

Figure 5:
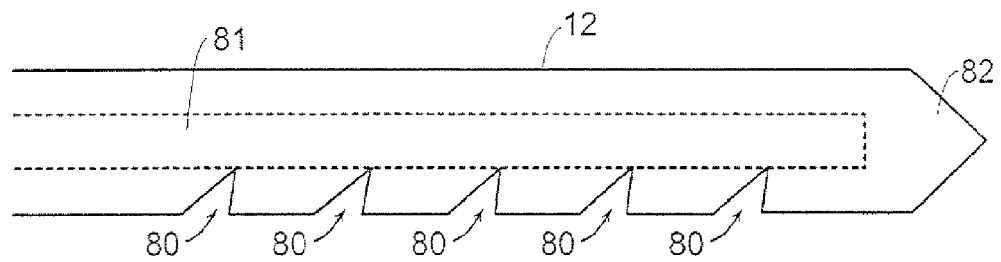
FIG. 5 is a side view of an alternative embodiment of the microneedles in accordance with the invention.

In certain embodiments, as illustrated in FIG. 5, the microneedles 12 can have holes 80 on the side-walls at various and/or multiple positions along the length through which fluid can be transmitted in conjunction with a bore or hollow pathway 81, combined with the opening 73 (FIG. 4) or with a solid tip 82 (FIG. 5). There can be from one to 20 or more holes 80. The spacing between the holes 80 is approximately in the range of 100 μm to 2 mm.

The microneedles 12 may be manufactured from a variety of materials and by a variety of methods. Representative materials include metals, ceramics, semiconductors, organics, biodegradable and non-biodegradable polymers, glass, quartz, and various composites. Representative methods include micro-fabrication techniques. In the illustrated embodiment, the microneedles 12 are made of medical grade stainless steel, such as 304 stainless steel. Stainless steel microneedles are advantageous because they are durable, semi-flexible, and have the mechanical strength to endure insertion into the stratum corneum. They can be cut from readily available, relatively inexpensive commercial stock via a chemical saw, or any suitable technique, to the desired dimensions, and ground to the desired tip geometry.

The microneedles 12 have an inner diameter of about 10 μm to 100 μm, an outer diameter of 30 μm to 250 μm, and a length of approximately 5 mm to 10 mm. In the illustrated embodiment, each of the microneedles has an inner diameter of about 54 μm, and an outer diameter of about 108 μm. Other embodiments use microneedles with an inner diameter of about 100 μm and outer diameter of about 175 μm.

Figure 4A:
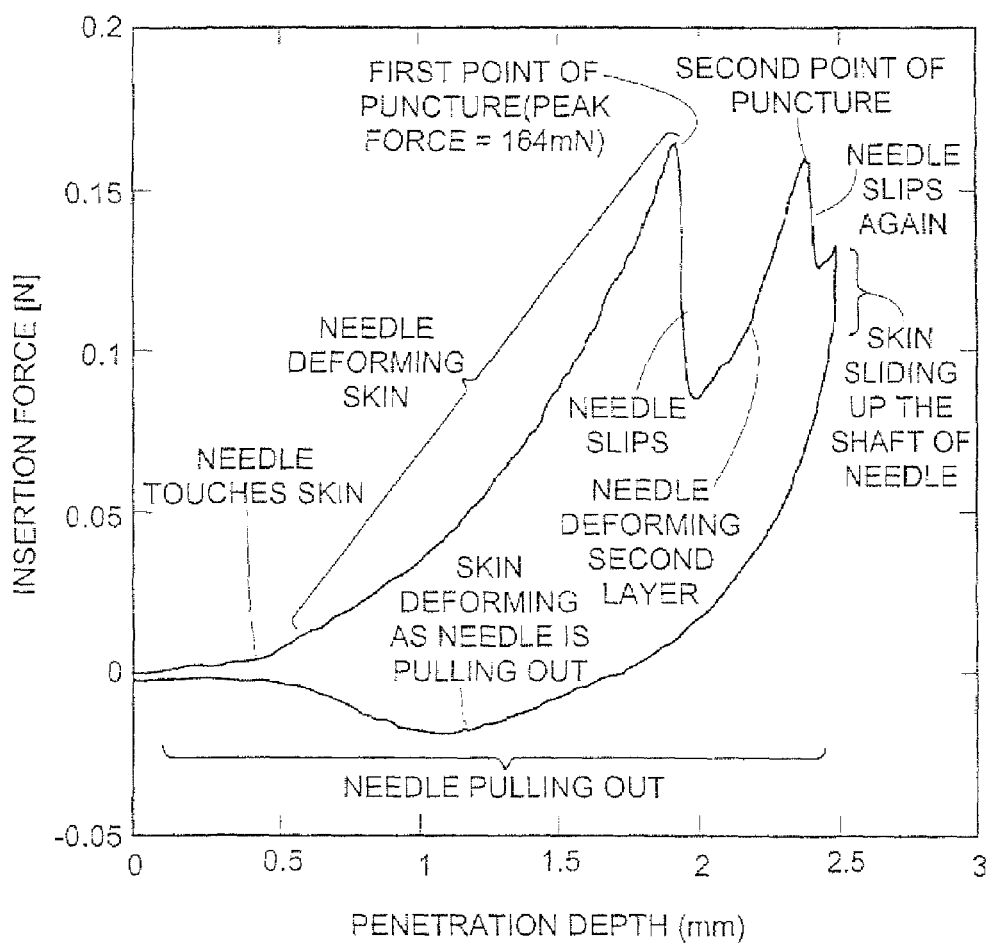
FIG. 4A is a graph of the insertion force of a microneedle versus the penetration depth of the microneedle.

Referring to FIG. 4A, there is shown a plot of insertion force of a needle versus penetration depth, illustrating the skin and needle behavior as described by the various labels. After the needle touches the skin, the skin is deformed until a first point of puncture, after which the needle slips. Subsequently, the needle deforms the second layer of skin until a second point of puncture, after which the needle slips again.

Then the skin slides up the shaft of the needle. As the needle is pulled out, the skin is also deformed, as shown in the bottom portion of the graph.

Figure 4B:
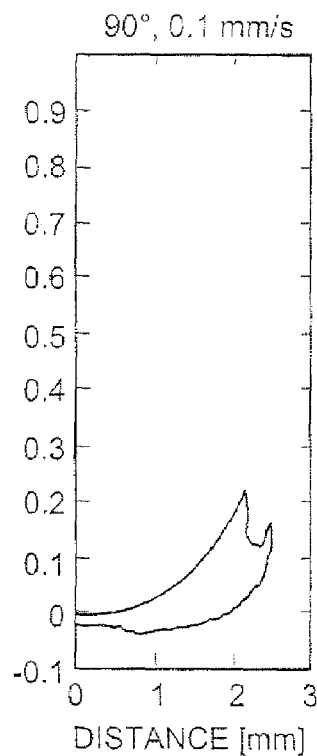
FIG. 4B-4E is a sequence of graphs of the insertion force of a microneedle versus the penetration depth of the microneedle for different diameter needles.
Figure 4C:
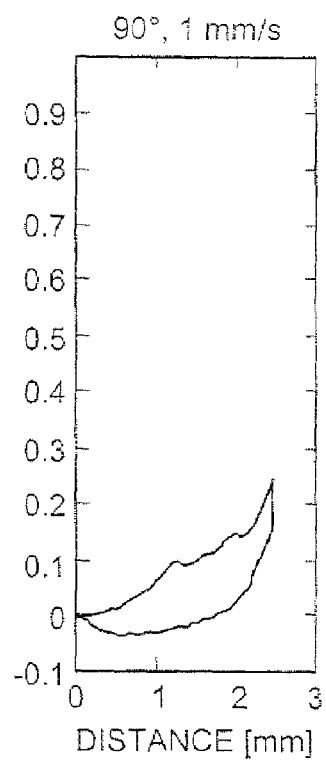
Figure 4D:
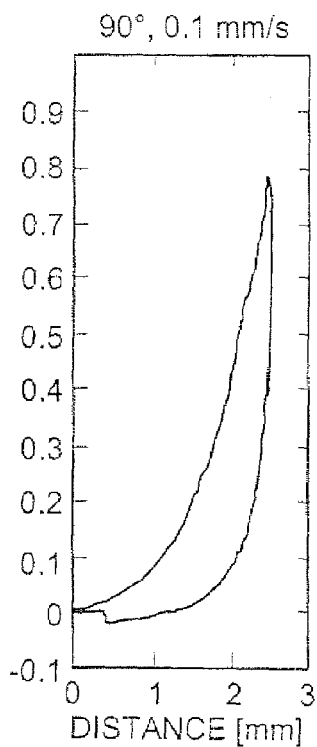
Figure 4E:
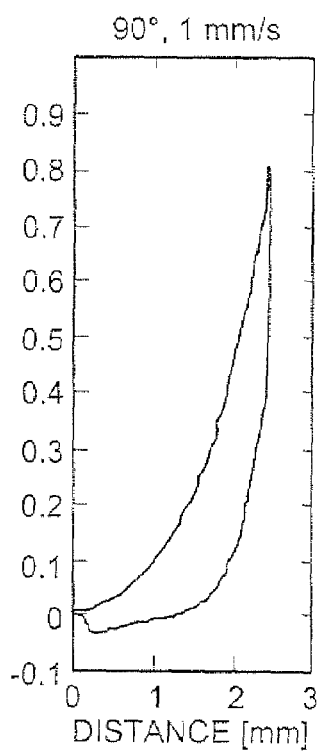

Turning now to FIGS. 4B-E, a sequence of graphs illustrate the insertion force [N] versus penetration depths [mm] for 100 μm (top graphs, FIGS. 4B and 4C) and 570 μm (bottom graphs, FIGS. 4D and 4E) needles that are at an angle of 90° with respect to the surface of the skin, and for needle insertion velocities of 0.1 and 1.0 mm/s. As is evident from the figures, the smaller needles have significantly smaller penetration forces. The figures also show that the velocity of needle insertion does not significantly affect the penetration forces. The peak insertion force for a 100 μm needle into the skin at a 90° angle at a velocity of 1 mm/s is approximately 250 mN (FIG. 4C), while that for a velocity of 0.1 mm/s is about the same (FIG. 4B).

The microneedles 12 can also be coated on the outside, the inside, or both. Coatings can cover part or all of either or both surfaces. Coatings can be selected from, but are not limited to, the group consisting of lubricants, chemical or biological reaction elements, and preservatives.

The microneedles may be made of one or more rows of microneedles of uniform or varying dimensions and geometries, with uniform or varying spacing, at uniform or varying projection angles, and any combination thereof. In the embodiment above, the set of microneedles form a circular array of four microneedles. The array has a radius of approximately 5 mm to 20 mm. In the illustrated embodiment, the radius is about 12 mm. In another embodiment, the set may include more than one circular array of microneedles. In yet another embodiment, the microneedles are arranged in an X by Y array, where X may or may not equal Y.

The rigid section or shell 48 of the reservoir 46 is made from stainless steel, in which case the microneedles 12 are metal welded or soldered to the shell 48. Alternatively, the shell can be made of glass, such as Type I or Type II high purity glass, or polymer. Each of the flexible membranes 28 and 42 is approximately 20 μm to 500 μm, preferably 100 μm, thick, and is made from a deformable elastopolymer such as silicone rubber, or any other suitable flexible material. In some implementations, the reservoir 46 is filled with one or more pharmaceuticals for delivery to the patient, and then sealed.

In the illustrated embodiment, the reservoir 46 is a single-chambered, hollow container with a maximum fill thickness of approximately one to 5 mm, preferably about 2 mm, and a volume capacity approximately in the range of 100 μl to 5 ml.

In the device 10, the microneedles 12 are in contact with the pharmaceutical in the reservoir 46. However, there can be a semi-permeable membrane filter, or valve placed between the reservoir 46 and the openings at the ends 13 of the microneedles. The filter can serve to purify the substance, or remove a selected material from the substance entering or leaving the reservoir. A filter can also contain a binding partner to the selected material, thereby capturing or trapping that material during the transport. The binding partner can be specific or nonspecific. A valve is useful in preventing leakage as well as in precisely releasing a set amount of substance. The valve is also useful to prevent backflow of a collected fluid through the microneedles 12. In some embodiments, a microvalve is opened in each microneedle 14 to allow movement of fluid for delivery or collection. For example, the microvalve could be embedded in the microneedles 12 or be part of the reservoir 46. Alternatively, a non-permeable membrane, covering for example the end of the microneedle opening into the reservoir, can be breached to allow the fluid movement.

Rather than being a hollow chamber, in some embodiments the reservoir 46 can be a porous matrix, single or multi-chambered, or any combination thereof. Each chamber can be the same or may differ from any or all of the others. For example, the reservoir 46 can have one chamber that contains a reagent and into which fluid is drawn through the microneedles 12. A reaction might then occur in this first chamber, the results of which might trigger manual or automatic release of a substance from a second chamber through the microneedles into the skin.

The reservoir 46 is easily loaded with a substance to be delivered. The reservoir 46 may be prefilled with the substance, and then incorporated with the device 10 before delivery. Loading can occur before or after association of the reservoir 46 with the microneedles 12. As mentioned earlier, the formulation can be one or more non-liquid drugs (for example, that have been dehydrated) that may be preloaded into the reservoir 46, and then reconstituted before delivery. In some embodiments, the inside of the reservoir 46 is coated with a material prior to assembly of the reservoir. The coating can have one or more purposes, including, but not limited to, aiding flow so that the substance exiting or entering the reservoir moves smoothly and/or does not leave behind droplets, serving as a reactant used for detecting the presence or absence of a particular material in the fluid, and/or serving as a preservative.

When the transport device 10 is used to deliver drugs, the reservoir 46 stores one or more drugs in one or more chambers to be delivered to the target site. The reservoir 46 can be filled with the desired drug through an opening situated opposite the placement of the microneedles 12. Alternatively, the desired drug can be drawn up into the reservoir 46 through the microneedles or the desired drug can be placed within the reservoir 46 when it is sealed.

When the transport device 10 is used to obtain samples from the patient, the reservoir 46 stores, in one or more chambers, one or more biological samples drawn from the patient. The device can include one or more elements directed at securing the sample within the reservoir during removal of the device from the skin. These elements might include valves, flaps and the like.

Although the illustrated embodiment uses adhesive to secure the device 10 to the skin, alternative mechanisms for securing the device 10 on the skin are available that include, but are not limited to, one or more straps, tape, glue, and/or bandages. The outer casings of the control unit 14, and the base portion 16 can be made of any stiff material, such as, but not limited to, stainless steel and other hard metals, plastics, woven or matted stiffened fibers, cardboard, and wood.

The actuators 24 and 38 need not operate as vapor generators. In some configurations, the actuator or pump 38, and optionally the actuator 38, operates by an electrochemical reaction, in particular electrolysis of water ($H_2O$) that converts water into hydrogen ($H_2$) and oxygen ($O_2$) gas. There are two electrochemical reactions taking place: oxidation is occurring at the anode according to the reaction $$2H_2O(l) \rightarrow O_2(g) + 4H^+(aq) + 4e^-$$

and reduction is occurring at the cathode according to the reaction $$2H_2O(l) + 2e^- \rightarrow H_2(g) + OH^-$$

To keep the numbers of electrons balance, the cathode reaction must take place twice as much as the anode reaction. Thus, if the cathode reaction is multiplied by two and the two reactions are added together, the total reaction becomes $$6H_2O(l)+4e^- \rightarrow 2H_2(g)+O_2(g)+4H^+(aq)+4OH^-(aq)+4e^-$$

The H$^+$ and OH$^-$ form H$_2$O and cancel species that appear on both side of the equation. The overall net reaction therefore becomes $$6H_2O(l) \rightarrow 2H_2(g)+O_2(g)$$

Hence, three molecules (1 O$_2$, 2 H$_2$) are produced per 4 electrons. That is, the number of moles of gas created by electrochemical decomposition of water as described by the following equation is $$n_{gc}=n_{ge}/(eN_A)=7.784 \times 10^{-6} \text{ mol/C}$$

where n$_{ge}$ is the number of molecules of gas produced per electron put into the system, ¾, e is the charge of one electron, and N$_A$ is Avogadro's number. This conversion results in a large volume change of over, for example, three orders of magnitude, which is harnessed to expel the drug from the reservoir 46. When the conversion of water to hydrogen and oxygen occurs, the expansion compresses the flexible membrane 42, expelling the drug and any carriers or other compounds or solvents out of the reservoir 46 through the microneedles 12.

Figure 6:
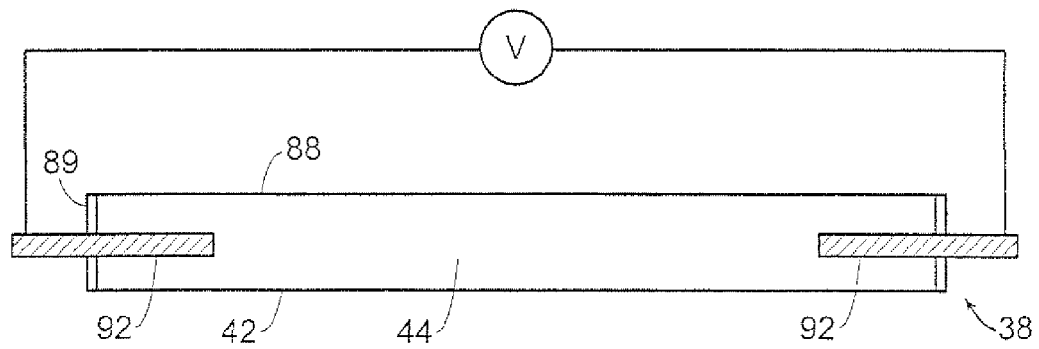
FIG. 6 is a side view of an alternative embodiment of an actuator of the transdermal transport device shown in FIGS. 1A-1D.

Referring in particular to FIG. 6, there is shown the actuator 38 by itself for illustrative purposes when it operates by an electrolytic process. The actuator 38 includes a rigid shell 88 connected to the membrane 42 with a flexible bellow 89, or any other suitable expandable material, defining the chamber 44. The chamber 44 contains, for example, 1 μl to 1 ml of water with 1 M of Na$_2$SO$_4$ or NaOH. To initiate the electrolytic process, a current, I, is applied to two electrodes 92 positioned within the chamber 44. Each electrode 92 can be solid or a mesh. The mesh configuration provides a larger surface area to initiate the decomposition process. The electrodes can be made of stainless steel, platinum, or platinum/iridium gauze, such as Alfa Aesar #40934, or any other suitable material.

Figure 7:
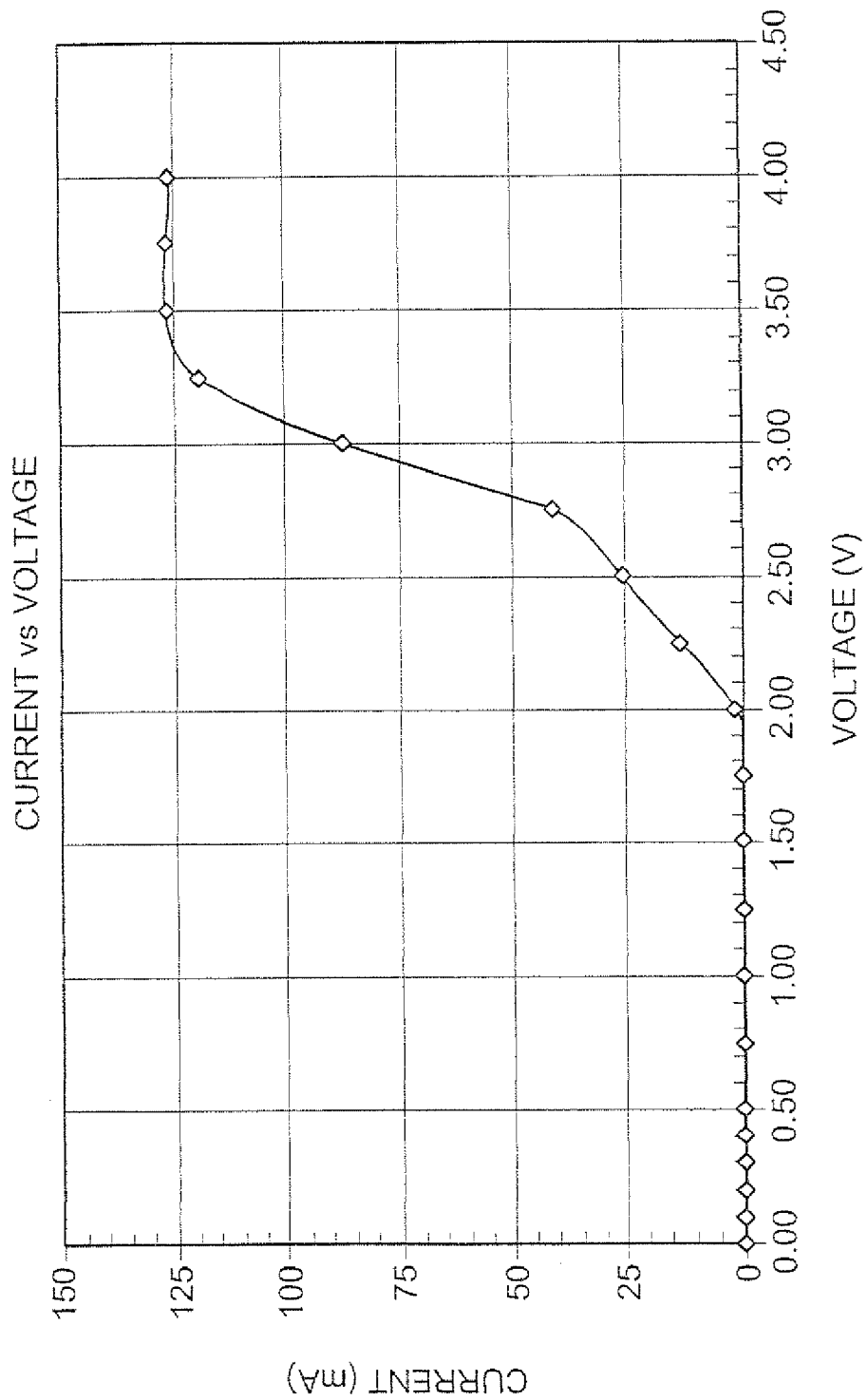
FIG. 7 is a graph of the voltage requirements of the actuator shown in FIG. 6.

Referring to the graph depicted in FIG. 7, there is shown a representative voltage to current relationship for the actuator 38. In the present embodiment, the operating current is about 0.95 A, and hence, the operating voltage is about 3 V. The electrolytic process can be easily stopped and if desired initiated again, and this process can be repeated to precisely control the expansion rate of the chamber 44 and hence the drug delivery rate of the device 10.

Alternatively or additionally, the actuator 24 can be an electrolytic actuator, as described above in reference to the actuator 38. The actuators 24 and/or 38 can be micro-electric motors, such as, for example, Lorentz force or electrostatic motors, or operate by chemical or electrochemical reactions, conducting contractile polymers, shape memory alloys, or any other suitable mechanism to facilitate the transport of the pharmaceutical. Alternatively or additionally, the actuators can include mechanical or organic members, such as microvalves or permeable membranes, respectively, to further control transport rates. The actuators 24 and 38 can also be any other suitable micro-mechanism, such as motors, levers, pistons, solenoids, magnetic actuators, and the like, for controlling the motion of the flexible membranes 28 and 42 to provide precise and controlled delivery of compounds and/or collection of body fluids.

In some embodiments, the shell 48 of the reservoir 46 is not rigid, but instead is formed from a conducting polymer, such as polypyrrole, which contracts (usually in one direction) under the application of a low voltage current. In essence, the conducting polymers act like human muscle, that is, they contract lengthwise. The force produced per area of these polymers is about 1 to 10 Mpa, which is about a factor of 10 greater than that of human muscles. The change in length of these polymers is about 2%. Contraction of the conducting polymer forces the drug and any carriers or other compounds or solvents out of the reservoir 46.

When the device is used to collect samples, reversible actuators such as the conducting polymer pump system can be used in reverse to facilitate transport from the target area to the reservoir 46. For example, initial application of a low voltage current compresses the shell 48, emptying the reservoir 46. While the reservoir is in its contracted state, the device 10 is applied to the target site. The voltage is then disrupted to allow the polymer to expand to its natural state. Expansion of the reservoir 46 creates a vacuum inside the reservoir 46, which causes fluid to be drawn into the reservoir.

Another embodiment of the actuators 24 and 38 is a shape memory alloy or contractile polymer wrapped around a circle. The actuator forms a twist that is guided along a thread so that there is a linear (vertical) motion which places a force on the drug vial 40, thereby expelling the drug from the reservoir 46. The actuator is returned to its initial retracted state by one of many available means that includes but is not limited to shape memory alloys, springs, and super-elastic metal.

Any of the foregoing embodiments, as well as any other applicable to the situation, could be synchronized with the impedance sensor 52, discussed in detail below, so that the drop in impedance, upon penetration through the stratum corneum, triggers the pumping action of the actuator 38, such as the electrolytic, chemical reaction, polymer contraction actuators, or an electric motor or any other actuators used in the device 10.

In certain embodiments, the device 10 is provided with contoured, drilled tunnels or guide sleeves through which the microneedles 12 are guided into the skin.

In some embodiments, the transport device 10 includes an oscillator system 59, made from, for example, a piezoelectric crystal, to assist the insertion of the microneedles 12. The oscillator system can be an independent system, integrated with the actuators, or some combination thereof. Preferably, the microneedles are vibrated at about 10 kHz in the direction of the penetration motion. A potential advantage of using such an oscillator system 59 is that less force may be required to penetrate the skin.

As discussed above, the device 10 includes electrical sensors, such as the impedance sensor 52 which detects penetration of the stratum corneum. That is, the sensor 52 signals when the desired insertion of the microneedles 12 have been achieved. The determination of the location of the microneedle tip(s) within or through the stratum corneum allows for delivery of a complete, predetermined dose to the patient at a location amenable for absorption by the patient's body.

This is accomplished by measuring impedance of the tissue as the microneedles proceed through it. As the stratum corneum creates a high level of impedance, and the tissue beyond the stratum corneum only provides a relatively low level of impedance, impedance is monitored to determine when the microneedles have passed through the stratum corneum. At that point insertion may be stopped so as to avoid penetrating the skin layer containing nerves and capillaries.

Figure 8:
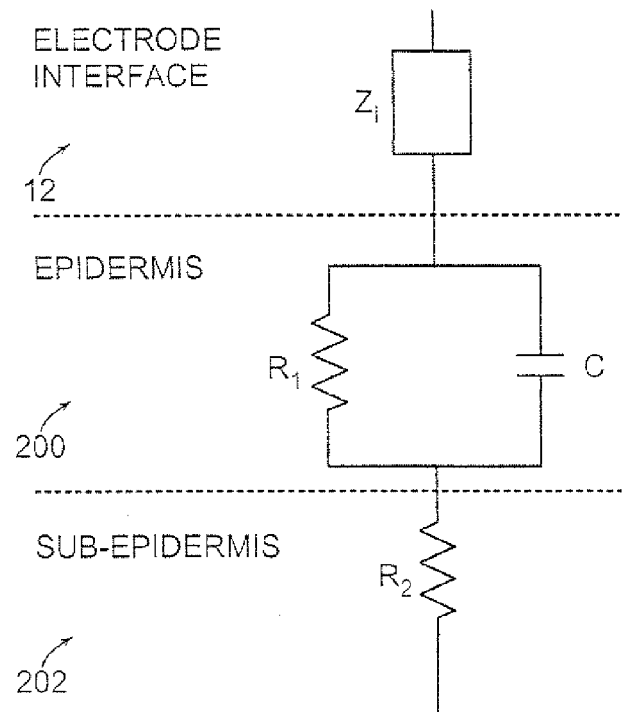
FIG. 8 is schematic of a circuit formed with electrodes of an impedance sensor of the transdermal transport device shown in FIGS. 1A-1D and the skin of a patient.
Figure 8A:
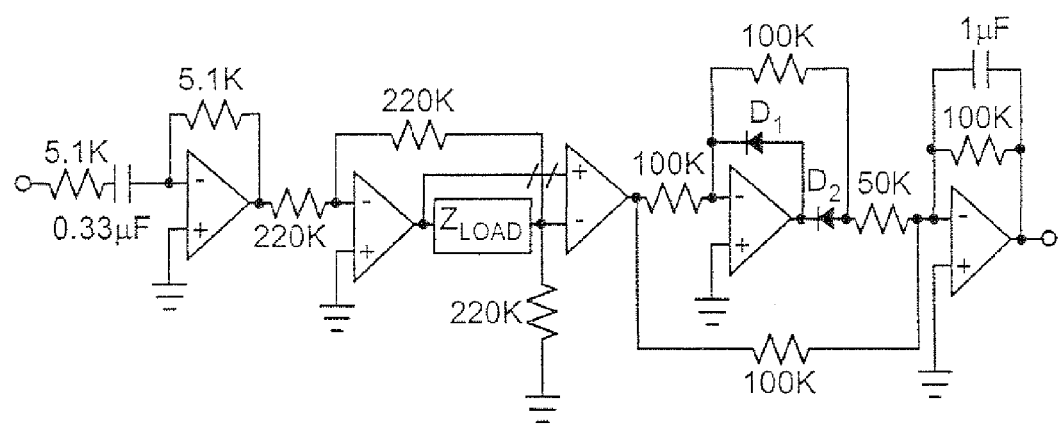
FIG. 8A is schematic diagram of a circuit used for the impedance sensor in accordance with the invention.

In particular, as illustrated in FIG. 8, a low voltage circuit is formed with two of the microneedles 12 acting as electrodes. Because the dry stratum corneum of the epidermis 200 acts as a capacitive barrier while the sub-epidermal layers 202 are well conducting, the impedance of the circuit drops as the microneedles pierce through the stratum corneum 200. The change in impedance is by one or more orders of magnitude and reliably indicates when the microneedles have pierced through the stratum corneum 200. Furthermore, at less than 1 Volt, the voltage stimulus is not felt by the subject. Note also that the microneedles 12 are electrically isolated from the base. An illustrative embodiment of a circuit diagram of the circuit used here is shown in FIG. 8A, where the $Z_{load}$ represents the unknown impedance.

Figure 9:
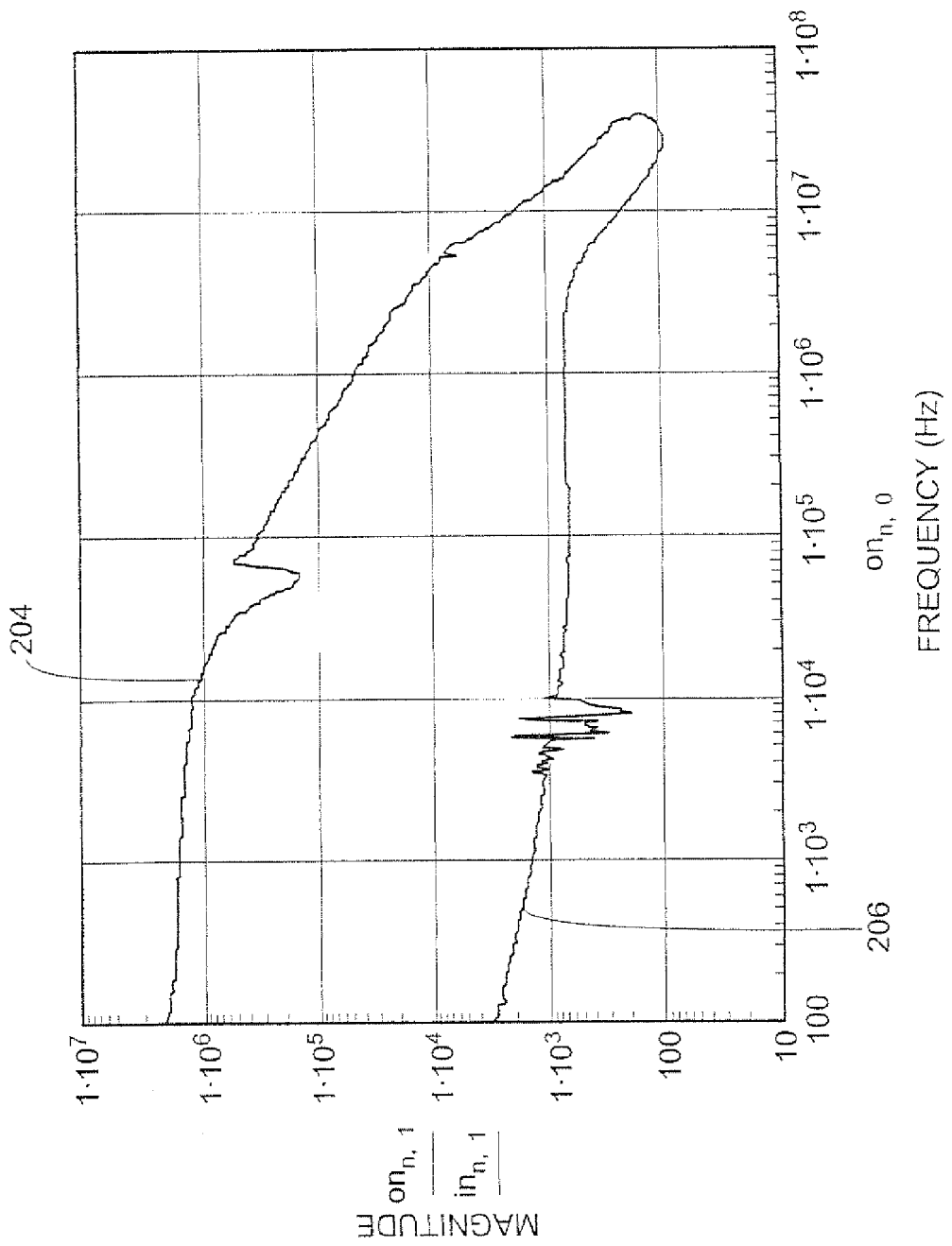
FIG. 9 is a graph of the magnitude of the impedance measured by the impedance sensor of FIG. 8 versus frequency.
Figure 9A:
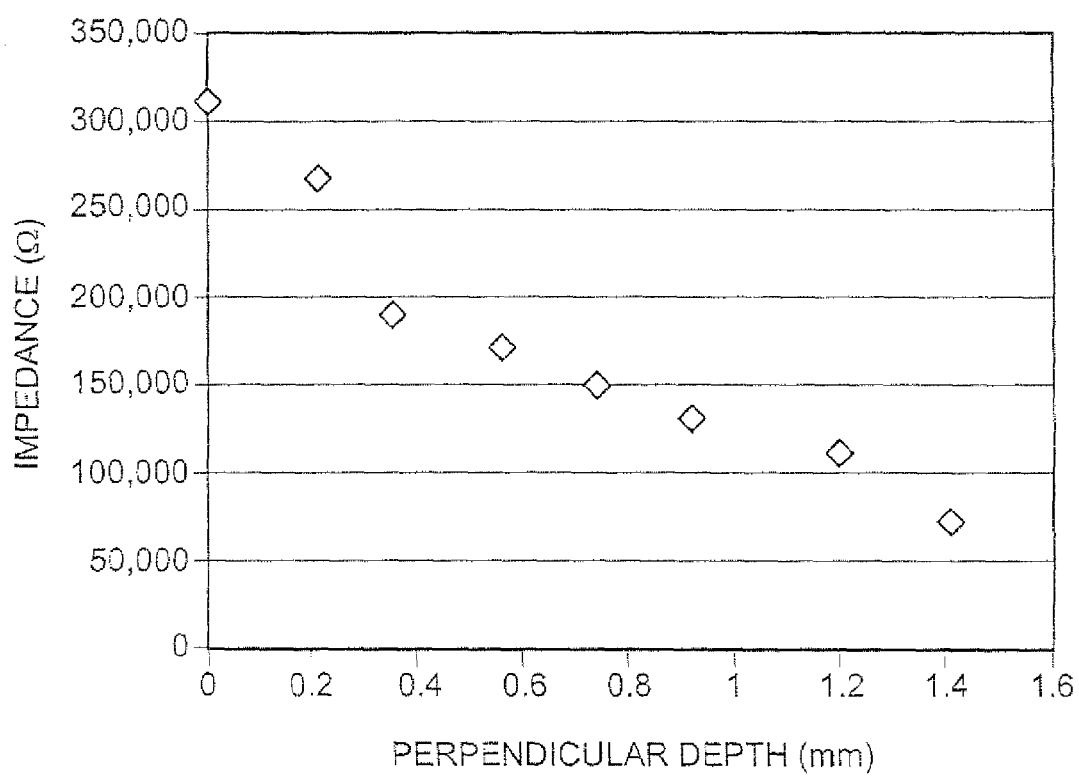
FIG. 9A is a graph of the impedance versus the penetration depth.

As an example, impedance measurements of pig skin is illustrated in FIG. 9. The top portion 204 of the graph illustrates the measured impedance of pig skin over a frequency range before a microneedle penetrates the stratum corneum and the bottom portion 206 represents the measured impedance after the microneedle has penetrated the stratum corneum. As one can see, the difference between the two portions 204 and 206 of the graph can be over three orders of magnitude. Turning also to FIG. 9A, there is shown a plot of impedance versus the perpendicular depth of penetration into the skin, which illustrates that the penetration into the skin produces smaller impedances.

Rather than sweeping over a frequency range, the input signal of the impedance sensor 52 can be set at one frequency. The input signal can be a square wave generated by an embedded processor such as a TI-MSP430F149IPM, produced by Texas Instruments of Dallas, Tex. Certain characteristics of this chip are that it draws 35 µA when active, and less than 1 µA in a low power mode, and has a 64 pin PQFP package, a 1.8 to 3.6 V power supply, 8 analog to digital converters, 60 kbytes of flash memory, 2 kbytes of RAM, 2 16-bit timers, and an on-chip comparator. Alternatively, a processor such as a TI-MSP430F110IPW can be used. This chip draws 35 µA when active and less 11 µA in low power mode, and includes a 20 pin TSSOP, 1.8 to 3.6 V power supply, 1 kbyte of flash memory, 128 bytes of RAM, and a 16-bit timer. The output signal for any of these chips can be pulse width modulated, and the impedance sensor 52 can be provided with a log transformer to compress the output signal to within the range of the analog to digital converter of the processor.

As mentioned earlier, in certain embodiments, a glucose sensor, or other suitable sensor, is associated with the transport device 10. In these embodiments, fluid is withdrawn from the patient through the microneedles 12 into one of a multiplicity of reservoir chambers 46. The glucose sensor is at least partially positioned in one of the chambers, where it can detect the concentration of glucose in the fluid. Information from the glucose sensor is read and interpreted by the operator of the device 10, for example, with the use of the display 55 of the control unit 14, who can then activate another chamber of the reservoir to deliver the appropriate amount of insulin to bring the glucose concentration to an appropriate level. Alternatively, the procedure can be automated so that the glucose sensor reads the glucose concentration in the fluid, and, based on that concentration, sends a signal, such as an electronic signal, to the other chamber, "telling" that chamber whether or not to deliver insulin through a set of microneedles, and how much insulin to deliver.

In any of the above described embodiments, one or more controllers such as the programmable microprocessor 22 located in the control unit 14 can control and coordinate the actuators, pumps, sensors, and oscillators. For example, the controller 22 can instruct the actuator 38 to pump a specified amount of drug into a patient at a specified time. The specified amount may be the full amount contained in the reservoir 46 or a partial amount. Thus, the device is able to inject a partial or full amount of drug incrementally over a particular time period. One controller may control the operation of the base unit 16, while another controller controls the operation of the control unit 14. For instance, when the control unit 14 functions as an applicator, it may have a separate controller, and another controller may be located within the base unit 16 to control its operations. Alternatively, the control unit 14 and base unit 16 can function as a single unit, in which case a single controller controls their operations. In such implementations, an optional applicator can be used to attach the control unit 14 and base unit 16 to the patient, and the optional applicator may be provided with an additional controller.

While this invention has been particularly shown and described with references to preferred embodiments thereof, it will be understood by those skilled in the art that various changes in form and details may be made therein without departing from the scope of the invention encompassed by the appended claims.

What is claimed is:

1. A transdermal transport device, comprising:
   a reservoir including at least two reservoir chambers, a first reservoir chamber including a sensor for detecting concentration of a substance and a second reservoir chamber for holding a formulation of an active principle;
   an array of needles, each needle having a bore in fluid communication with the reservoir;
   a first actuator that drives the array of needles into a body, the first actuator being reversible to withdraw the needles from the body; and
   a second actuator that withdraws a fluid from the body through the needles into the first reservoir chamber; the second actuator being reversible to deliver the formulation of the active principle from the second reservoir chamber to the body in response to detected concentration of the substance in the withdrawn fluid.

2. The transdermal transport device of claim 1 wherein the sensor is at least partially positioned in the first reservoir chamber.

3. The transdermal transport device of claim 1 wherein the sensor is arranged to detect glucose concentration in the withdrawn fluid.

4. The transdermal transport device of claim 3 wherein the formulation of the active principle is insulin, the amount of insulin pumped into the body depending on the glucose concentration.

5. The transdermal transport device of claim 1 further including one or more controllers to control the second actuator to pump a specified amount of the formulation of the active principle.

6. The transdermal transport device of claim 1 wherein the plurality of needles are positionable in a retracted state when the first actuator is de-energized.

7. The transport device of claim 1 further comprising one or more controllers, wherein at least one of the first and the second actuators is under the direction of the one or more controllers.

8. The transport device of claim 1 wherein at least one of the first and the second actuators includes a vapor generator.

9. The transport device of claim 1 wherein at least one of the first and the second actuators operates by a chemical reaction process or electrochemical process.

10. The transport device of claim 1 further comprising an oscillator which causes the plurality of needles to vibrate to reduce the force required to advance the needles through the surface of the body.

11. The transport of claim 10 wherein the oscillator is a piezoelectric crystal.

12. The transport device of claim 1 wherein the first actuator is contained in a control unit, and the second actuator an plurality needles are contained in a cartridge, the control unit and the cartridge being separate connectable units with respect to one another.

13. A method for transporting a formulation of an active principle through a surface of a body, the method comprising:
   advancing an array of needles into the body, each needle having a bore in fluid communication with a reservoir, the reservoir including at least two reservoir chambers, a first reservoir chamber including a sensor for detecting concentration of a substance and a second reservoir chamber for holding a formulation of an active principle;
   withdrawing a fluid from the body into the first reservoir chamber;
   detecting the concentration of the substance in the withdrawn fluid using the sensor in the first reservoir chamber; and
   in response to detected concentration of the substance in the withdrawn fluid, pumping the formulation of the active principle from the second reservoir chamber into the body using the second actuator.

14. The method of claim 13 wherein the sensor is at least partially positioned in the first reservoir chamber.

15. The method of claim 13 further including detecting glucose concentration in the withdrawn fluid.

16. The method of claim 14 wherein the formulation of the active principle is insulin, the amount of insulin pumped into the body depending on the glucose concentration.

17. The method of claim 13 further including controlling the second actuator to pump a specified amount of formulation of the active principle.

18. The method of claim 13 wherein the plurality of needles are positionable in a retracted state when the first actuator is de-energized.

19. The method of claim 13 further including controlling at least one of the first and the second actuators under the direction of one or more controllers.

20. The method of claim 13 wherein at least one of the first and the second actuators includes a vapor generator.

21. The method of claim 13 further including operating at least one of the first and the second actuators by a chemical reaction process or electrochemical process.

22. The method of claim 13 further including vibrating the plurality of needles to reduce the force required to advance the needles through the surface of the body.

23. The method of claim 22 further including vibrating the plurality of needles using a piezoelectric crystal.

* * * * *